United States Patent [19]
Anderson et al.

[11] Patent Number: 6,086,543
[45] Date of Patent: Jul. 11, 2000

[54] FINE NEEDLE AND CORE BIOPSY DEVICES AND METHODS

[75] Inventors: Scott C Anderson, Sunnyvale; Roberta Lee, Redwood City; James W. Vetter, Portola Valley, all of Calif.

[73] Assignee: Rubicor Medical, Inc., Redwood City, Calif.

[21] Appl. No.: 09/104,069

[22] Filed: Jun. 24, 1998

[51] Int. Cl.[7] .................................................. A61B 5/00
[52] U.S. Cl. ............................................................ 600/567
[58] Field of Search ............................ 600/562, 564–567; 606/170

[56] References Cited

U.S. PATENT DOCUMENTS

| | | |
|---|---|---|
| D. 337,821 | 7/1993 | Tan . |
| 4,099,518 | 7/1978 | Bayliz et al. ............................ 600/567 |
| 4,210,146 | 7/1980 | Banko . |
| 4,643,196 | 2/1987 | Tanaka et al. ........................... 600/566 |
| 4,651,752 | 3/1987 | Fuerst . |
| 4,664,128 | 5/1987 | Lee . |
| 4,697,600 | 10/1987 | Cardenas et al. . |
| 4,926,877 | 5/1990 | Bookwater . |
| 4,971,067 | 11/1990 | Bolduc et al. . |
| 4,989,614 | 2/1991 | Djeter, Jr. et al. . |
| 5,111,828 | 5/1992 | Kornberg et al. . |
| 5,133,359 | 7/1992 | Kedem . |
| 5,148,813 | 9/1992 | Bucalo . |
| 5,183,052 | 2/1993 | Terwilliger . |
| 5,188,118 | 2/1993 | Terwilliger . |
| 5,199,441 | 4/1993 | Hogle . |
| 5,241,969 | 9/1993 | Carson et al. . |
| 5,246,011 | 9/1993 | Caillouette . |
| 5,257,632 | 11/1993 | Turkel et al. . |
| 5,353,804 | 10/1994 | Kornberg et al. . |
| 5,413,115 | 5/1995 | Baldwin . |
| 5,488,958 | 2/1996 | Topel et al. . |
| 5,499,989 | 3/1996 | LaBash . |
| 5,505,211 | 4/1996 | Ohto et al. . |
| 5,522,398 | 6/1996 | Goldenberg et al. . |
| 5,526,821 | 6/1996 | Jamshidi . |
| 5,526,822 | 6/1996 | Burbank et al. . |
| 5,615,690 | 4/1997 | Giurtino et al. . |
| 5,645,537 | 7/1997 | Powles et al. . |
| 5,649,547 | 7/1997 | Ritchard et al. . |
| 5,660,186 | 8/1997 | Bachir . |
| 5,885,226 | 3/1999 | Rubinstein et al. .................... 600/564 |

OTHER PUBLICATIONS

W. Phil Evans Core Biopsy: Guns And Needles, p. 55 to 106, Chapter 6 of Interventional Breast Procedures, Churchill Livingstone, Inc. 1996.

*Primary Examiner*—Max Hindenburg
*Attorney, Agent, or Firm*—Young Law Firm, P.C.

[57] ABSTRACT

A device to retrieve a specimen from soft tissue includes a cannula having an axial lumen, a sharpened distal tip and at least one tissue urging feature extending along at least a portion of the length of the cannula. As the cannula rotates, the tissue urging feature urges the specimen into the lumen. A vacuum may be used to assist in drawing the specimen into the lumen. The tissue urging feature may be continuous or discontinuous, such as a spiral thread within the lumen of the cannula, spirally wound raised features or a combination of raised and recessed features. The lumen may include a proximal section having a larger diameter than a distal section thereof. A soft tissue biopsy method includes a step of advancing a rotating cannula-stylet combination into a mass of soft tissue, the cannula having a distal center lumen and a proximal center lumen aligned with the distal lumen, the proximal lumen having a larger diameter than the diameter of the distal lumen. The stylet is at least partially retracted when the combination is near the target site within the soft tissue. The tissue within the distal lumen is then twisted and compressed as the tissue progresses therethrough as the cannula rotates and advances to and through the target site. The twisted and compressed tissue is thereafter at least partially untwisted and decompressed as it enters the proximal lumen. The tissue is then collected from the proximal lumen.

31 Claims, 8 Drawing Sheets

FINE NEEDLE AND CORE BIOPSY DEVICES AND METHODS

BACKGROUND OF THE INVENTION

1. Field of the Invention

The present invention pertains to methods and devices for performing fine needle aspiration biopsies and large core biopsies. In particular, the present invention relates to fine needle aspiration and large core biopsy devices having enhanced cell and/or tissue collection features and to improved cell and/or tissue collection methods.

2. Description of the Related Art

To diagnose suspicious palpable or non-palpable masses in soft tissues, such as breast tissue, often requires that a sample thereof be obtained. Currently available cell and tissue extraction techniques include fine needle aspiration and large core techniques.

Fine needle aspiration (hereafter FNA) is a process wherein a 20 to 25 gauge needle attached to a syringe is inserted through the skin to the target lesion. While pulling back on the syringe plunger to create a vacuum, the needle is moved back and forth at least 5 to 10 times in a translational and rotational movement, targeting multiple sites within the lesion. The movement of the needle within the target lesion, as well as the applied suction, hopefully causes cells within the lesion to be dislodged and forced into the internal lumen of the needle. The needle may then be retracted from the tissue. The collected cells may then mounted on slides and examined by a cytopathologist for possible malignancy.

Core biopsy techniques, on the other hand, utilize a larger gauge needle, typically 14 to 18-gauge. Whereas FNA techniques generally collect only individual cells, core biopsy devices and techniques collect a much larger sample and generally preserve the tissue architecture. In core biopsy, the most popular means for retrieving a core sample utilizes a spring-loaded, hand held automated gun is used to retrieve the sample. The gun includes an inner needle having a tissue-receiving slot and an outer cutting needle surrounding the inner needle, both spring loaded. When the gun trigger is depressed, the inner needle is shot through the soft tissue to a predetermined distance, generally referred to as the "throw" of the gun. The inner needle includes a slot on the side thereof that is designed to receive the tissue to be severed. Immediately after the tissue enters the tissue-receiving slot, the outer needle is released, severing the tissue and leaving a tissue core inside the slot of the inner needle. The assembly is then retracted and the core specimen sent for histopathological analysis.

Both FNA and core biopsy devices, however, suffer from a number of disadvantages. Turning first to fine needle aspiration, the success rate of FNA procedures appears to be heavily dependent upon the skill and degree of experience of the operator. Indeed, at least 30% of FNA procedures performed on breast tissue yield inadequate or non-diagnostic cell samples. Non-diagnostic samples are those in which, for example, no cells are present in the material extracted from the breast, those in which only fat cells are retrieved or those in which an insufficient number of breast epithelial cells are present for the cytopathologist to adequately characterize the retrieved sample. Failure to retrieve a diagnostic quality sample does not alleviate the need for a positive diagnosis, however; and in those instances in which FNA fails to return a proper sample, the procedure must be repeated. Alternatively, a more invasive procedure must be performed to retrieve the desired sample. Moreover, the translational movement of the FNA needle, repeated at least 5 to 10 times, may be painful to the patient and traumatic to the tissue mass within which the biopsy is performed. FNA, for at least these reasons, can prove to be a frustrating procedure to an inexperienced physician, who may, therefore, opt to carry out the relatively more invasive core biopsy procedure.

Large core biopsy techniques and devices have enjoyed a comparatively greater acceptance than have FNA devices and techniques. Core biopsy needles are typically about 14 gauge, are typically shot into the target lesion under great acceleration, and retrieve a comparatively larger amount of tissue than do FNA needles. Because of the large gauge of the needles and the high acceleration under which they are introduced into the mass to be biopsied, the procedure is more invasive, painful and psychologically traumatic. Moreover, it is often necessary to repeat the procedure four to six times to obtain an adequate specimen, whether the biopsy is carried out under stereotactic, ultrasound or manual guidance. Additionally, there are instances in which the needle may not penetrate and may even bounce off particularly dense tissue. The procedure, therefore, is often a painful and frightful experience for the patient. Indeed, the loud report of the automatic biopsy gun (often compared to that of a large staple gun) as the trigger is depressed and the needle is fired invariably makes the patient (and sometimes the physician) flinch or startle, which may cause the needle to miss its target.

Other problems occasionally encountered with core biopsy techniques include failure of the outer cutting needle to completely advance over the inner needle, due to highly dense tissue. Removal of the device may then be difficult, as compressed tissue may have entered into the slot in the inner needle without being completely severed from the mass. Removal of the device in such cases may lead to significant hematomas, swelling and damage to collateral tissue. Moreover, core biopsy techniques may be contraindicated in cases wherein augmentation prostheses are present in the breast.

Safety is also a concern with conventional FNA and core biopsy techniques, as the thrusting motion inherent in FNA procedures and the high needle accelerations of core biopsy procedures can lead to accidental puncture wounds to the patient or the surgeon. Such accidental puncture wounds increase the possibility of accidental contact with harmful viruses, such as the HIV or hepatitis B virus. Moreover, such thrusting motion and/or high acceleration may lead to a bending of conventional cannulas and/or stylets, particularly when dense tissue is present. Such bending may injure the patient and may be a contributing factor in the relatively high failure rate of FNA and related biopsy procedures.

What are needed, therefore, are improved cell and tissue collection methods and devices that would allow a safe and consistent collection of diagnostic quality specimens. Indeed, although FNA biopsy techniques have somewhat fallen into disfavor, primarily due to their poor success rate, FNA remains the least invasive technique for rapidly screening soft tissue, such as breast tissue, for malignancies. There has been a long felt need, therefore, to more consistently obtain diagnostic quality biopsy specimens, using minimally invasive and thus minimally traumatic means and techniques. What are also needed are cell and tissue collection methods and devices that are not as dependent upon the skill of the operator as are FNA biopsy techniques. Moreover, practitioners and patients alike have long felt the need for cell and tissue collection methods and devices that are less traumatic to surrounding soft tissue and that result in fewer complications, such as bruising and swelling. There has also been a long felt need for diagnostically effective alternatives to automatic core biopsy guns, alternatives that preferably do not depend upon the violent release of spring loaded needles.

SUMMARY OF THE INVENTION

In accordance with the above-described objects and those that will be mentioned and will become apparent below, a device to retrieve a specimen from soft tissue, according to an embodiment of the present invention, comprises:

a cannula having an axial lumen and a sharpened conical distal tip;

discontinuous tissue urging means extending along at least a portion of a length of the axial lumen, the tissue urging means urging the specimen into and along the axial lumen upon rotation of the cannula; and drive means for rotating the cannula.

According to further embodiments, the axial lumen may comprise a distal and proximal section, the proximal section having a greater diameter than the distal section, the tissue urging means extending along at least a portion of a length of the distal section of the axial lumen. The drive means may comprise means for axially oscillating the cannula during rotation thereof A stylet may also be included, the stylet being adapted to fit within the axial lumen of the cannula. The discontinuous tissue urging means may be disposed in a generally spirally shaped configuration about a circumference of the axial lumen. The discontinuous tissue urging means may include a plurality of through cut slots. The discontinuous tissue urging means may include either discontinuous raised features rising from an interior surface of the axial lumen or discontinuous spiral threading within the axial lumen. The tissue urging means may include spirally wound deformations in both the outer surface of the cannula and in the axial lumen thereof.

A device to retrieve a specimen from soft tissue, according to another preferred embodiment of the present invention, comprises:

a cannula having an axial lumen, the axial lumen including a distal and proximal section, the proximal section having a greater diameter than the distal section; and tissue urging means integral to the cannula and extending along at least a portion of a length of the distal section of the axial lumen, the tissue urging means urging the biological specimen first into the distal section and then into the proximal section upon rotation of the cannula.

In other embodiments, the tissue urging means may be continuous or discontinuous. The tissue urging means may be disposed in a generally spiral-shaped configuration about the circumference of the cannula. The tissue urging means may include a plurality of through cut slots or may include spiral threading of the axial lumen of the cannula. The pitch of the spiral threading may be selected within the range of about 10 to about 300 threads per inch. The tissue urging means may include a spirally wound raised feature rising from the surface of the axial lumen.

The tissue urging means may include spirally wound deformations in both the outer surface of the cannula and in the axial lumen thereof. Such tissue urging means may be formed by applying a localized and radially-directed force to the outer surface of the cannula in a spiral pattern over at least a portion of the length of the cannula, thereby simultaneously forming a recessed spiral pattern on an outer surface of the cannula and a corresponding raised spiral pattern within the axial lumen. Alternatively, such tissue urging means may be formed by applying a localized and radially-directed force to a surface of the axial lumen in a spiral pattern over at least a portion of an axial length thereof, thereby simultaneously forming a recessed spiral pattern within the axial lumen and a corresponding raised spiral pattern on the outer surface of the cannula.

A part-off feature may be attached to the conical distal tip. The part-off feature may include a portion of a sharpened semi-hemispherical member fitted to the conical distal tip. A stylet may be included, which stylet is adapted to fit within the axial lumen. The device may further include an adapter connected to a proximal end of the cannula; and vacuum means for creating a vacuum within the axial lumen, the vacuum means being attached to the adapter. A motorized drive means may also be included to selectively rotate the cannula. The drive means may include means for axially oscillating the cannula upon rotation thereof The conical distal tip may be sharpened on the outer diameter of the cannula and/or on the inner diameter of the cannula.

According to a still further preferred embodiment, a soft tissue biopsy method comprises the steps of:

advancing a rotating cannula-stylet combination into a mass of soft tissue, the cannula having a distal center lumen and a proximal center lumen aligned with the distal lumen, a diameter of the proximal lumen being larger than a diameter of the distal lumen;

at least partially retracting the stylet when the combination is near a target site within the soft tissue;

twisting and compressing the tissue within the distal lumen as the tissue progresses through the distal lumen upon rotation and advancement of the cannula to and through the target site;

at least partially untwisting and decompressing the twisted and compressed tissue as the tissue enters the proximal lumen; and collecting the expanded tissue from the proximal lumen.

A step of at least partially parting off the twisted tissue may be carried out prior to stopping the rotation of the cannula. The parting-off step may include a step of macerating tissue at a distal tip of the cannula by stopping the advancement of the cannula through the mass of soft tissue while continuing the rotation thereof. A step of imposing an oscillating axial movement on the cannula as the cannula rotates and advances through the target site may also be carried out.

BRIEF DESCRIPTION OF THE DRAWINGS

For a further understanding of the objects and advantages of the present invention, reference should be made to the following detailed description, taken in conjunction with the accompanying figures, in which.

DESCRIPTION OF THE PREFERRED EMBODIMENTS

Investigations into the underlying causes of failures of FNA biopsy techniques have revealed the following. It is believed that the primary causes of such failures likely are inadequate cellular material collection and misdirected sampling. Failure of FNA techniques due to misdirected sampling may be improved, it is believed, with greater experience on the part of the operator, coupled with ultrasonic guidance of the tip of the device to the lesion site. However, even when performed on surgical specimens, the failure rate of FNA biopsy techniques has been reported to be as high as 7%. This appears to indicate that the primary cause of failure of small bore techniques, such as FNA, is inadequate cellular mass retrieval.

It is believed that inadequate cellular mass retrieval, in turn, may be primarily caused by the following factors. The first of such factors is believed to be the failure of tissue to enter into the FNA needle. Typically, FNA biopsy procedures utilize conventional hypodermic needles. However, the beveled tips of conventional hypodermic needles are designed to cut through, rather than to core the tissue into which they are introduced. Function follows design in this case, in that conventional hypodermic needles are designed to aspirate bodily fluids, and not to collect solids. Conventional wisdom, however, teaches that the type and structure of the needle used in FNA procedures is of little importance. The second of such factors is believed to be the failure of the tissue entering such conventional FNA needles to remain therein as the needle is retracted. Indeed, as the needle is retracted, the specimen collected in the interior lumen of the hypodermic needle often slides back out again. This undesired loss of tissue specimen upon retraction of the needle is believed to occur for two reasons. The first is that the sample has often not been parted off from the surrounding tissue, and thus remains attached thereto. As the needle is retracted, the still-attached tissue is pulled in the opposite direction, causing it to slide out of the needle lumen. The second reason for loss of collected tissue is believed to be related to the extremely small vacuum force present within the internal lumen of the hypodermic needle used for the FNA procedure. Indeed, such vacuum typically produces a force on the order of about 0.001 pounds for a 25-gauge needle. Such weak force is often insufficient, by itself, to effectively keep the collected tissue within the needle lumen upon retraction thereof from the soft tissue mass.

The present invention is at least partly predicated upon these findings, and addresses the disadvantages of both conventional FNA biopsy and large core biopsy devices and methods. According to the preferred embodiments of the FNA and large core biopsy devices and methods of the present invention, an outermost cannula having a centered axial lumen and a sharpened conical distal tip is rotated, at least during the cell and/or tissue collection phases of the specimen collection procedures. The rotation of the cannula, according to the present invention, has several advantages. One such advantage is that the rotation of the cannula reduces the friction of its advancement through the tissue mass to be biopsied. Indeed, the rotation of the cannula, according to the present invention, reduces the effective axial friction of the tissue on the cannula over its entire length. This reduced axial friction, in turn, has several advantages. For large core biopsies, in which it is desired to collect comparatively large tissue samples, rotation of the cannula is believed to reduce the need for a high axial acceleration of the cannula through the tissue mass to be biopsied, such as breast tissue. Indeed, as the cannula and the sharpened edge of its conical distal tip rotate, the cannula advances readily through the tissue to be biopsied with low friction, effectively advancing though even dense tissue and/or lesions. High axial accelerations, in conventional core biopsy devices, were necessitated by the high friction of the often-dense tissue upon the collection and cutting needles. By reducing this high friction, the present invention correspondingly reduces the need for such high axial accelerations. According to the present invention, the collection of even large core specimens, therefore, no longer necessitates automatic core biopsy guns, which depend upon stored potential energy of internal springs to shoot needles into the tissue mass. The present invention, therefore, addresses several of the major disadvantages of conventional core biopsy techniques. For example, the reduced friction of the rotating cannula according to the present invention allows cell and/or tissue samples to be retrieved from soft tissue, such as breast tissue, by advancing the cannula slowly and deliberately, in contrast to the somewhat violent release of conventional automatic biopsy guns. Such advancement may be carried out under manual or stereotactic control, with our without ultrasonic guidance. This comparatively slow advancement of the rotating biopsy cannula, according to the present invention, greatly reduces the patient's startle or flinch response often associated with the loud trigger report of conventional spring-released biopsy guns. In turn, this leads to greater precision in targeting small lesions, as the patient is less likely to jump, move or startle in response to or in anticipation of the release of the springs of a conventional biopsy gun. Greater precision in the targeting of lesions, in turn, leads to a greater success rate in the collection of diagnostic quality specimens. Rotation of the cannula also increases the efficiency with which the sharpened conical distal tip slices through the tissue. The sharpened conical distal tip, unlike the beveled distal tip of conventional hypodermic needles, is believed to be highly effective in cutting through tissue and encouraging tissue to enter the center axial lumen. Indeed, as the distal-most surface of the cannula is both perpendicular to the axis of the cannula and highly sharpened, tissue is believed to be much more likely to enter into the axial lumen than it is with conventional hypodermic needles having beveled tips. Indeed, the rotating and sharpened edge of the conical tip is believed to operate in a manner similar to a hollow drill bit, cutting through the tissue with greater ease than conventional hypodermic needles that are rammed, at a great acceleration, into the tissue mass to be biopsied. A further advantage of a rotating outer cannula relates to the diameter of the cannula itself The rotation of the outer cannula, according to the present invention, acts to effectively stiffen the cannula structure, allowing the use of cannulas of smaller diameter, for both FNA and core biopsy procedures. Smaller gauge cannulas cause fewer complications and are less traumatic and painful than larger gauge needles.

The cell and/or tissue collection devices, according to the present invention, include a cannula comprising a center axial lumen, tissue urging means and a sharpened conical distal tip. In direct contrast to the widely held belief that the type of FNA needle utilized is of little importance, the present invention proposes a number of features that enhance the tissue collection success rate. Indeed, according to the present invention and as shown in the drawing figures, the tissue urging means, together with the rotation of the outer cannula, urge the tissue into the axial lumen, and encourage the tissue to remain therein. The urging means may be integral to the cannula or may be attached thereto.

FIGS. 1A through 5C depict a number of embodiments of cannulas according to the present invention, each with different tissue urging means. The cannulas illustrated in FIGS. 1A through 5C, depending upon the diameter, or gauge thereof, may be utilized to collect cells for cytological examination, or may be used to collect larger tissue samples for histological examination. For example, small gauge cannulas within the range of about 20 to about 25 gauge may be used for an FNA-like procedure to collect cells, whereas cannulas of about 14 to about 18 gauge may be utilized to collect tissue samples, the larger diameter allowing the architecture of the collected specimen to be preserved. It is to be understood, however, that such arbitrary divisions between FNA and core biopsy techniques, within the context of the present invention, tend to become blurred where these two ranges coincide. Indeed, as the methods and devices disclosed herein may be used to collect both cell and tissue specimens, the differences between FNA and core biopsy become less distinct, as compared to conventional FNA and core biopsy methods and devices.

Figure 1A:
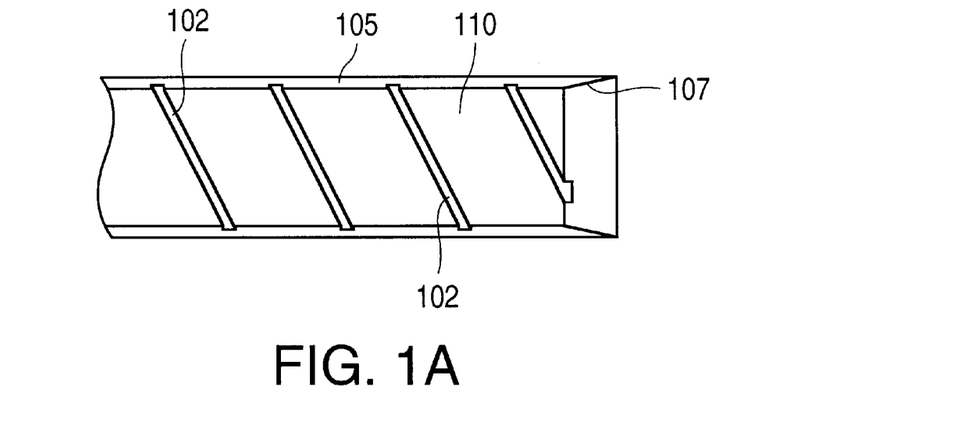
FIG. 1A shows a cross-section of an embodiment of a device for collecting cell and/or tissue specimen, according to an embodiment of the present invention.
Figure 1B:
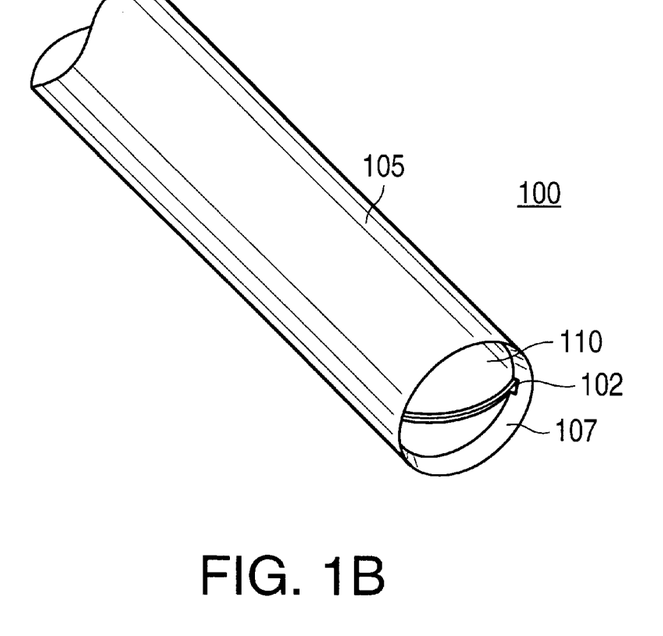
FIG. 1B shows a perspective view of the device for collecting cell and/or tissue specimen shown in FIG. 1A, according to the present invention.
Figure 2A:
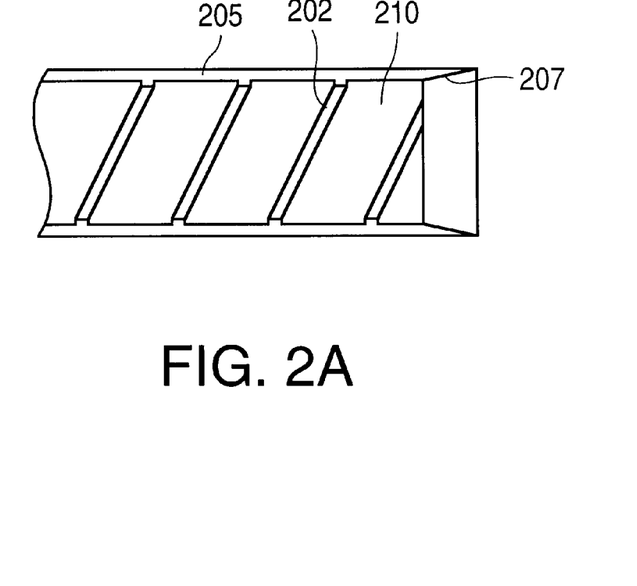
FIG. 2A shows a cross-section of another embodiment of a device for collecting cell and/or tissue specimen, according to an embodiment of the present invention.
Figure 2B:
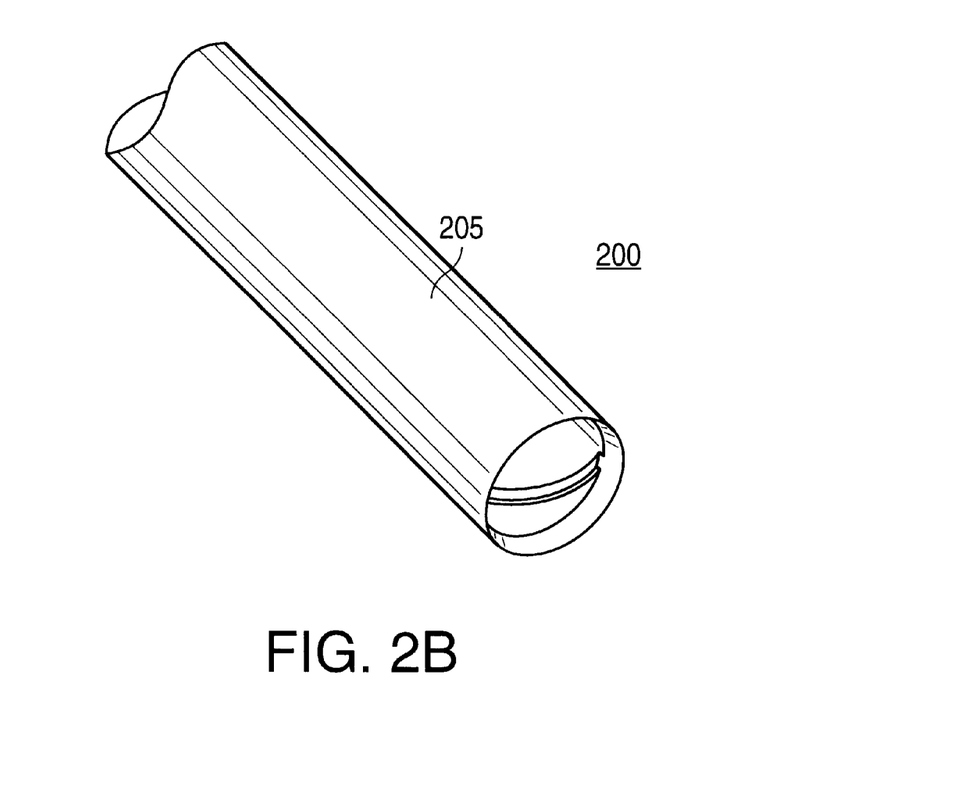
FIG. 2B shows a perspective view of the device for collecting cell and/or tissue specimen shown in FIG. 2A, according to the present invention.

Turning first to FIGS. 1A and 1B, FIG. 1A shows a cross-sectional view of the distal end region of a cannula according to the present invention. The distal end of the cannula 100 includes, as shown in both FIGS. 1A and 1B, a sharpened conical tip 107. The sharpened conical tip 107 is highly effective in slicing through even dense tissue as it rotates and encouraging tissue to enter the cannula's axial lumen 110. Tissue urging means 102 further encourage the tissue or cellular material entering the lumen 110 to advance therein. Indeed, the tissue urging means 102 help to draw the tissue specimen cut by the sharpened conical tip 107 into the lumen 110 as the cannula 100 is rotated. In the embodiment of the present invention shown in FIGS. 1A and 1B, this tissue urging means is shown as spiral threading within the cannula wall 105.

As the cannula 100 is rotated, tissue sliced by the sharpened conical tip 107 readily enters the lumen 110 and slides against the internal groove or thread 102. The thread 102 causes the tissue entering the lumen 110 to become twisted onto itself As the rotation of the cannula 100 continues, the thread 102 is believed to encourage the cut tissue to advance in the proximal direction as it is twisted into a generally helical shape within the lumen 110. Indeed, the twisting of the tissue entering the lumen 110 is believed to cause the tissue to become somewhat compressed and reduced in its outside diameter. This reduction in diameter is believed to aid the tissue in progressing through the cannula's internal lumen 110. Not only do the urging means 102 assist in the collection of cellular material within the lumen 110, but the urging means 102 also help in retaining the collected specimen within the lumen 110 as the cannula 100 is retracted. In conventional FNA devices, the collected specimen often slides out of the hypodermic needle's lumen, primarily due to the weak vacuum pressure present therein and the fact that the distal portion of the specimen has not been adequately parted off from the main tissue mass.

According to the present invention, however, the collected specimen is more likely to remain within the cannula's internal lumen 110. According to an embodiment of the present invention, as the rotation of the cannula 100 is stopped, the twisted and compressed tissue within the lumen 110 tends to untwist and expand somewhat, thereby exerting a radially directed force on the interior wall of the lumen 110. This force, coupled with the threading 102 of the lumen 110 (as opposed to the smooth surface of conventional hypodermic needle lumens) and the presence of a vacuum within the lumen 110 makes it more likely that the specimen collected within the cannula 100 will remain therein, even as the specimen is retrieved or the cannula 100 is entirely or partly retracted from the soft tissue mass. Therefore, the expanded tissue is held more firmly in the lumen 110 than it would be in conventional FNA devices, which facilitates its parting off from the main tissue mass. Alternatively, rather than merely stopping the rotation of the cannula 100, the radial expansion of the collected specimen within the lumen 110 may also be caused by reversing the direction of rotation of the cannula 100.

According to another embodiment of the present invention, the parting off of the collected specimen from the main mass is further facilitated by continuing the rotation of the cannula 100 while stopping its axial advancement through the tissue mass or the lesion site. In effect, when the advancement of the cannula 100 is stopped but the rotation thereof continues, the rotating sharpened edge of the conical tip 107 macerates the tissue directly distal to the tip 107 and facilitates its separation from the specimen collected inside the lumen 110. The pitch of the urging means thread 102 may be selected within a range of about 10 to about 300 threads per inch, depending on a number of factors including the intended speed of axial advancement, the type and density of tissue to be biopsied, as well as the rate of rotation of the cannula 100. Preferably, the pitch of the thread 102 should be about 150 to about 250 threads per inch.

The urging means 102, in the embodiment shown in FIG. 1A and 1B, are shown to be threads disposed in a spiral path within the internal lumen 110 of the cannula 100. In contrast, the urging means according to the present invention shown in FIGS. 2A and 2B comprise a spirally wound raised feature 202. The raised feature 202, therefore, projects from the internal wall 205 of the axial lumen 210 of the cannula 200. Preferably, the urging means, such as the spirally wound raised feature 202, extends from near the sharpened distal tip 207 to the proximal end region of the cannula 200, or a fractional portion of the axial length of the cannula 200. The pitch of the raised feature 202 may be selected within the same range as the thread 102 of FIGS. 1A and 1B. The raised feature 202 of the cannula 200 is believe to operate in a similar manner as the urging means 102, by twisting the specimen entering the lumen 210 onto itself and assisting its progress through the lumen 210 toward the proximal end thereof.

Figure 3A:
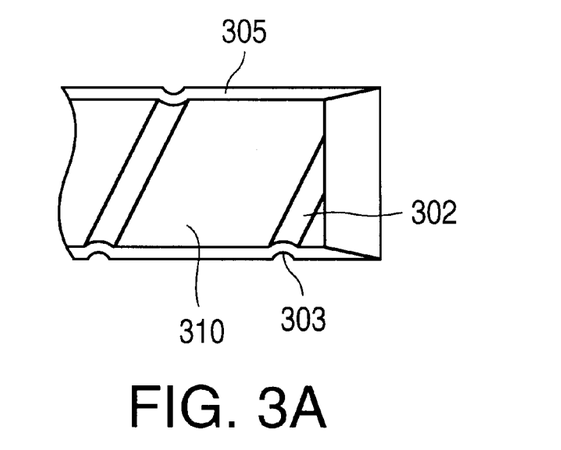
FIG. 3A shows a cross-section of a still further embodiment of a device for collecting cell and/or tissue specimen, according to an embodiment of the present invention.
Figure 3B:
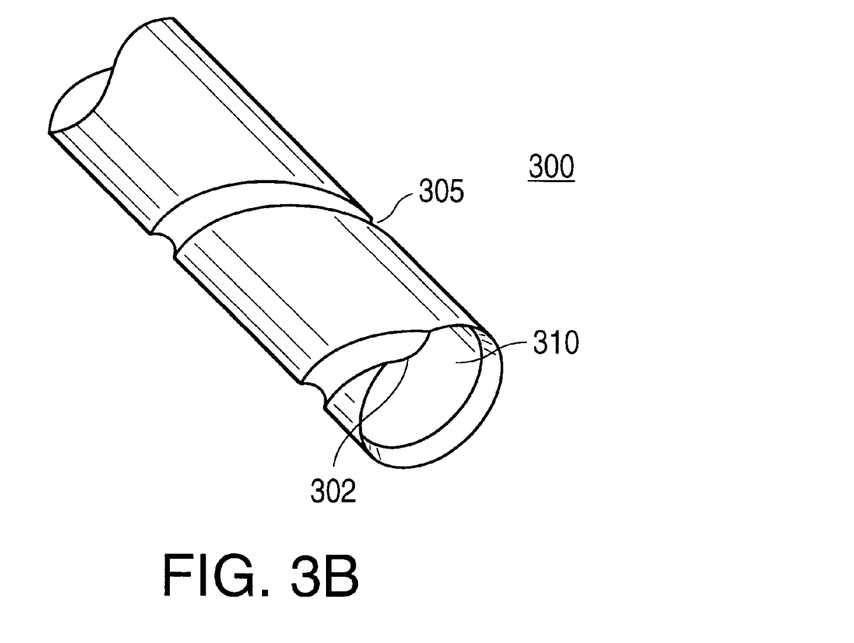
FIG. 3B shows a perspective view of the device for collecting cell and/or tissue specimen shown in FIG. 3A, according to the present invention.

The urging means of the cannula, according to the present invention, may assume any of a great variety of topographies. Indeed, a still further embodiment of a device for retrieving biological specimens from soft tissue according to the present invention is shown in FIGS. 3A and 3B. As shown in FIGS. 3A and 3B, both the internal and external surfaces of the cannula wall 305 include spirally wound features. As shown in FIGS. 3A and 3B, the lumen 310 of the cannula 300 includes urging means 302. The urging means 302, in the illustrated embodiment, are raised features similar to the urging means 202 in FIGS. 2A and 2B. In FIG. 3A and 3B, however, the external surface of the cannula 300 includes a spirally wound thread 303, while the lumen 310 includes a corresponding spirally wound raised feature 302. The thread 303 and the urging means 302 may be simultaneously formed by applying a localized and radially-directed force to the outer surface of the cannula 300 in a spiral pattern over at least a portion of the axial length of the cannula 300. Such a force should be sufficient to deform the exterior surface of the cannula wall 305 and to correspondingly create the raised feature 302 within the lumen 310. In this manner, a spirally wound recessed thread pattern 303 may be formed on the outer surface of the cannula wall 305, while simultaneously forming a corresponding raised spiral feature 302 within the axial lumen 310 of the cannula 300.

It is believed that the presence of a spirally wound thread 303 on the exterior surface of the cannula 300 aids the advancement of the cannula 300 through particularly dense or fibrous tissue. Indeed, the thread 303, in rotation, may help the cannula 300 to penetrate dense tissue, by reducing the friction of such tissue on the outer surface of the cannula. In turn, a successful advancement of the cannula 300 into dense lesions markedly enhances the ability of the device according to the present invention to retrieve diagnostically useful tissue specimens.

Alternatively, a radially directed force may be applied from within the lumen 310, to create a spirally wound thread feature within the lumen 310 and a corresponding raised feature on the exterior surface of the cannula 300. The urging means, in this case, being similar to those discussed relative to FIGS. 1A and 1B.

The urging means, according to the present invention, may be a continuous spirally wound feature, as shown in FIGS. 1A through 3B. Alternatively, the urging means may be discontinuous, forming a series of discrete topographical features within or on the lumen of the cannula and/or within or on the outer surface of the cannula. Such discontinuous urging means are preferably aligned in a spiral configuration along the length of the cannula or a fraction of the length thereof. Thus, each of the illustrative embodiments of the continuous urging means of the cannulas shown in FIGS. 1A through 3B instead may be implemented as a series of discrete features.

Figure 4A:
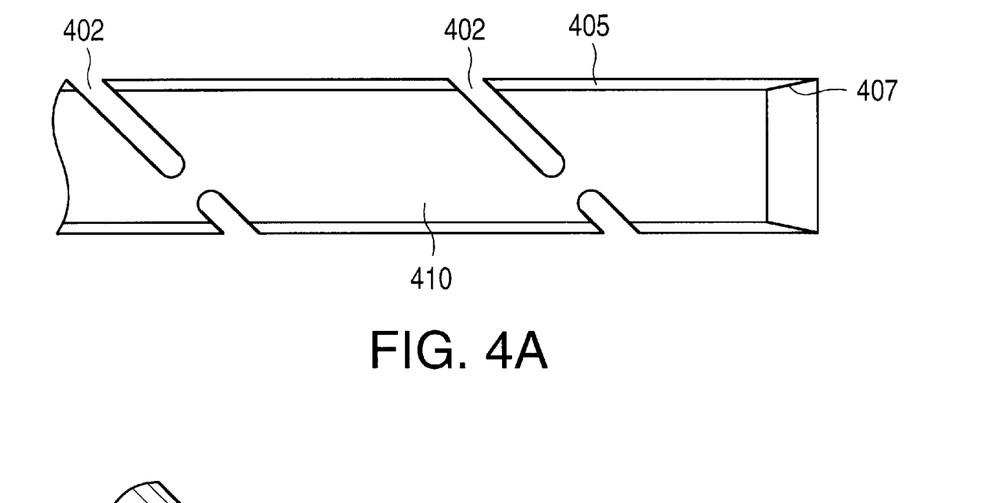
FIG. 4A shows a cross-section of yet another embodiment of a device for collecting cell and/or tissue specimen, according to an embodiment of the present invention.
Figure 4B:
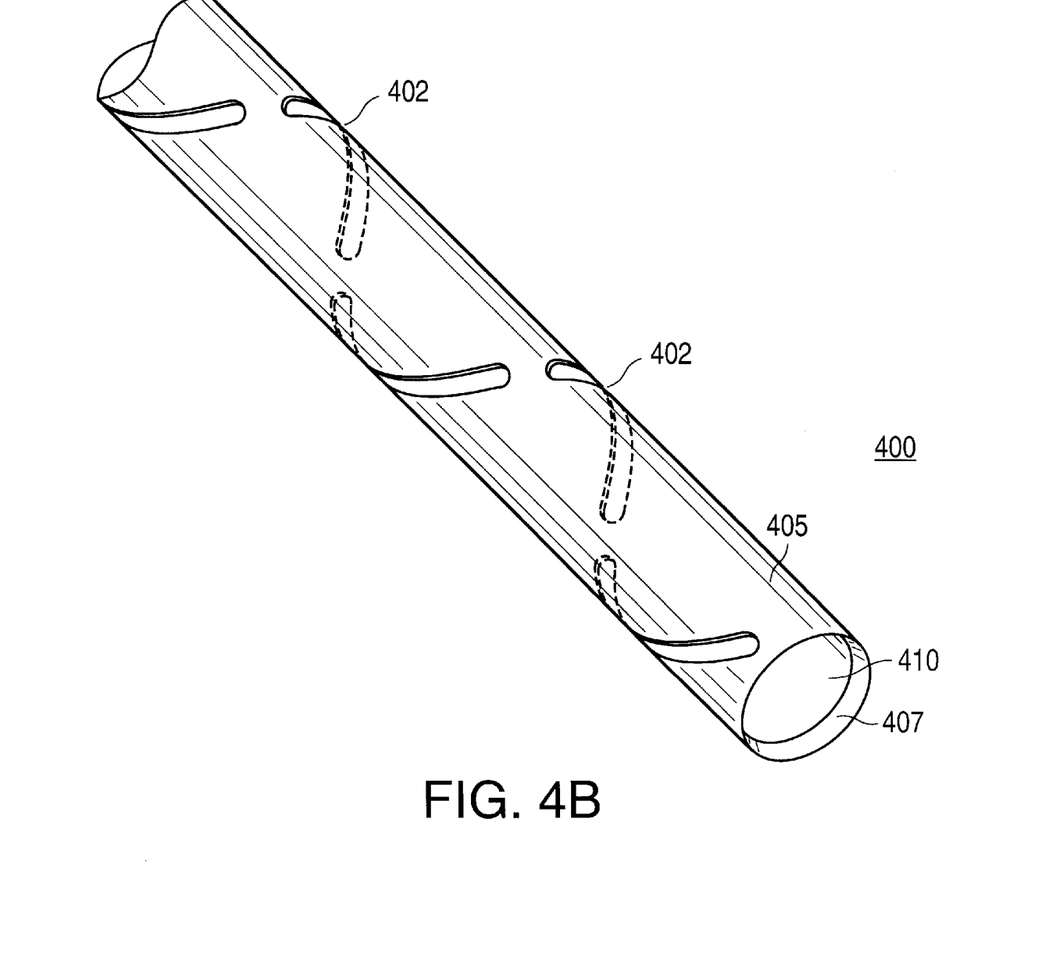
FIG. 4B shows a perspective view of the device for collecting cell and/or tissue specimen shown in FIG. 4A, according to the present invention.

A still further embodiment of the present invention is shown in FIGS. 4A and 4B. FIGS. 4A and 4B show a still further implementation of the urging means according to the present invention, as well as an embodiment wherein the urging means are discontinuous in nature. Indeed, FIGS. 4A and 4B show a cannula 400 comprising urging means including a series of spirally wound through cuts, collectively referenced by numeral 402. The urging means 402, as shown in FIGS. 4A and 4B, may be slot-shaped patterns that cut through the width of the cannula wall 405. These slot-shaped patterns are preferably a succession of patterns arranged in a spiral configuration around the circumference and down the axial length of the cannula 400. It is to be noted that the urging means 402 may alternatively be formed by through cuts having a shape other than that depicted in FIGS. 4A and 4B without, however, departing from the scope of the present invention. Care should be exercised, however, in forming the through cuts 402, to not unduly weaken the column strength of the cannula 400. Therefore, at least the number, width and pitch of the through cuts 402 should be carefully determined, depending upon the intended use, the thickness of the cannula wall 405 and the nature of the tissue to be biopsied, among other considerations. These factors will vary from application to application. In use, the urging means 402 help to draw the tissue entering the lumen 410 of the cannula 400 in the proximal direction, in a manner similar to the urging means illustrated in FIGS. 1A through 3B.

Figure 5A:
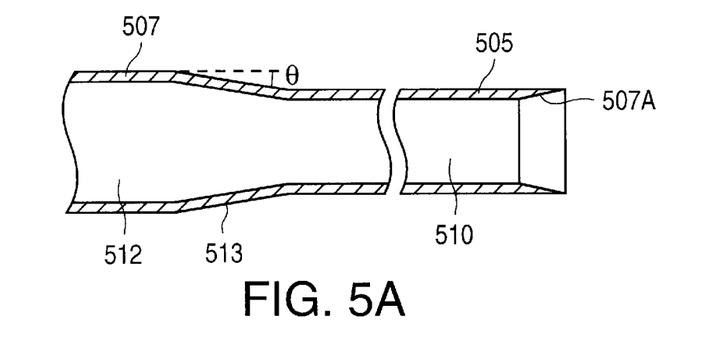
FIG. 5A shows a cross-section of a device for collecting cell and/or tissue specimen, according to an embodiment of the present invention.
Figure 5B:
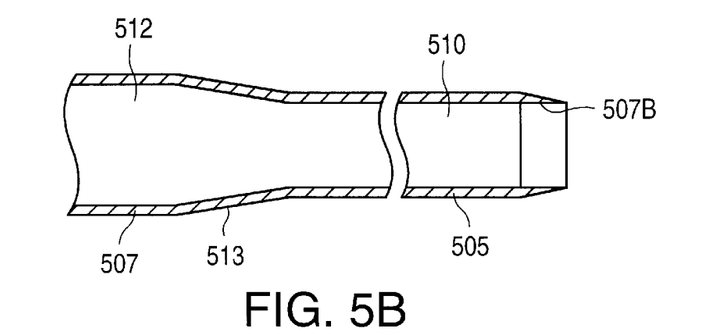
FIG. 5B shows a cross-section of a device for collecting cell and/or tissue specimen, according to another embodiment of the present invention.
Figure 5C:
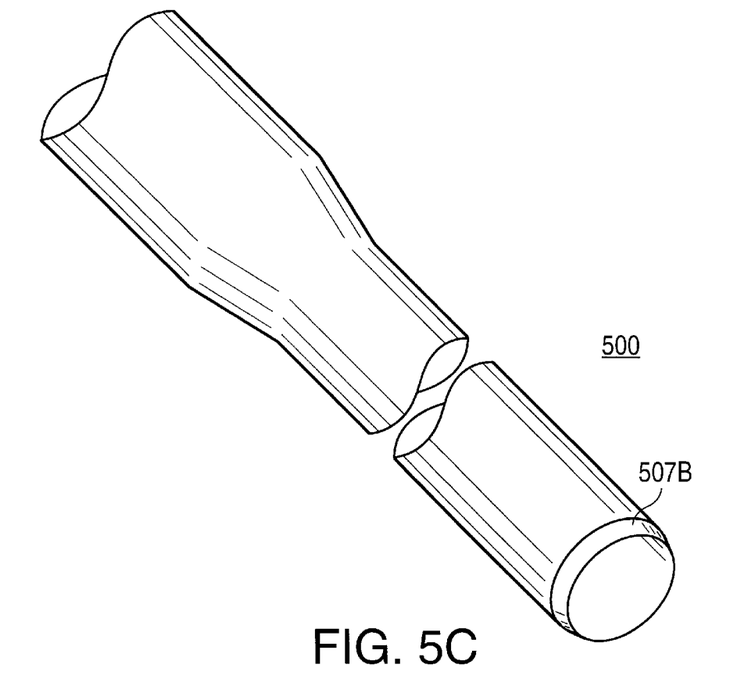
FIG. 5C shows a perspective view of the device for collecting cell and/or tissue specimen shown in FIG. 5B.

Further embodiments of the device and method according to the present invention for retrieving biological specimens from soft tissue are shown in the cross-sectional representations of FIGS. 5A and 5B and the perspective representation of 5C. As shown in FIG. 5A, the cannula includes a sharpened conical distal tip 507A and an axial lumen. The sharpened conical distal tip 507A is sharpened on its inner diameter. The axial lumen includes a proximal lumen 512 and a distal lumen 510, the proximal lumen 512 being axially aligned with the distal lumen 510. As shown in FIG. 5A, the diameter of the proximal lumen 512 is larger than the diameter of the distal lumen 510. Between the two cannula walls 505, 507 is a transitional wall section 513, which smoothly transitions between the cannula walls 505 and 507. The transitional wall section 513 may form an angle Θ with respect to the distal and proximal cannula walls 505 and 507. According to one embodiment of the present invention, the angle Θ may be selected within the range of about 1 to about 20 degrees. For example, the stepped cannula according to the present invention may swage from a 17 Ga. cannula to a smaller 18 Ga. cannula, with the transitional wall section 513 forming an angle Θ of about 5 degrees with respect to the distal and proximal cannula walls 505, 507, respectively. The cannula walls 505, 513 and 507 are preferably integral and homogeneous and may be formed of a material such as surgical grade surgical stainless steel, for example.

As shown in FIG. 5B, the sharpened conical distal tip 507B may alternatively be sharpened on its outer diameter. The remaining structural features of the cannula shown in FIG. 5B are similar to those of FIG. 5A, and have, therefore, been assigned identical reference numbers. The description of these features, therefore, is incorporated herewith in its entirety herewith. Advantageously, the sharpened conical distal tip 507B, being sharpened on the outer diameter of the distal cannula wall 505, does not substantially compress the tissue specimen entering the distal tip 507B of the cannula or cause additional resistance to forward (distally directed) movement. Indeed, the sharpened conical distal tip 507A necessarily somewhat compresses the tissue entering the tip, by reducing its volume. This reduction in volume is directly related to the thickness of the distal cannula wall 505. The sharpened distal conical tip 507B, on the other hand, maintains the same inner diameter over its entire length; namely, the inner diameter of the distal cannula wall 505. Therefore, the sample is substantially uncompressed as it enters the cannula tip 507B. That the tissue may be substantially uncompressed as it enters the distal tip 507B of the cannula assists the cannula in advancing through breast tissue, which may be locally dense and fibrous. Such a sharpened distal conical tip 507B, therefore, reduces the resistance to forward movement of the cannula and assists the physician in advancing the cannula to and through the site of interest. Such a rotating cannula is believed to be particularly effective in obtaining samples from mobile lesions. Mobile lesions are lesions (in breast tissue, for example) that are relatively harder than the softer surrounding tissue. Such mobile lesions may be pushed out of the way by a conventional bioptic needle that is advanced by a pushing or thrusting motion. According to the present invention, however, the forward resistance of the cannula is decreased, by virtue at least of its rotation and the rotating cutting edge of the sharpened conical distal tip of the cannula. Such structure and method of use is also believed to allow the use of a smaller gauge cannula than was previously possible with conventional bioptic devices. It is to be understood that the embodiments of FIGS. 1A, 1B, 2A, 2B, 3A, 3B, 4A, 4B and FIG. 6 may also incorporate a conical distal tip sharpened on the outer diameter of the cannula, as shown at 507B in FIG. 5B, instead of the distal tip sharpened on the inner diameter of the cannula shown therein. The cannula wall 505 of FIGS. 5A and 5B may advantageously incorporate any of the tissue urging means 102, 202, 302/303 and 402 of FIGS. 1A, 1B; 2A, 2B; 3A, 3B and 4A, 4B, respectively.

The proximal lumen 512 defined by the cannula wall 507, according to the present invention, receives the tissue sample collected in the distal lumen 510 as the cannula 500 is rotated. The tissue specimen, therefore, is urged first into the distal section and then into the proximal section upon rotation of the cannula. The comparatively larger diameter of the proximal lumen 512 allows the collected tissue entering therein to decompress somewhat, thereby facilitating retrieving the collected specimen from the cannula, after retraction thereof from the breast or other soft tissue.

The embodiments of the present invention shown in FIGS. 1A, 1B, 2A, 2B, 3A, 3B, 4A, 4B and FIG. 6 may also incorporate a transitional wall segment 513 and a cannula wall 507 defining a proximal lumen 512 of comparatively larger inner diameter than the lumen defined by distal portion of the cannula. Moreover, whereas the cannula wall 505 defining the distal lumen 510 may include topographic features such as tissue urging means, the cannula wall 507 is preferably smooth, including smooth inner and outer walls. By virtue thereof, the comparatively larger inner diameter of the proximal lumen 512 and the smooth interior surface of cannula wall 507 act in concert to further facilitate extraction of the collected sample from the cannula 500 after the core sample is collected.

According to an embodiment of the method of the present invention, the cannula 500 is inserted into the soft tissue, the cannula 500 being in full contact with the tissue mass to be biopsied over at least a portion of its length. The cannula 500 is rotated, at least when traversing the lesion site to be biopsied. The rotation of the cannula 500 eases its advancement through the lesion and the rotating cutting edge of the distal tip 507A or 507B efficiently slices therethrough, enabling the specimen to be collected within the distal lumen 510. As the specimen progresses through the distal lumen 510, it is twisted and compressed, by virtue of the urging means of the cannula wall 505 and/or the geometry of the sharpened conical distal tip 507A or 507B. The compressed and twisted tissue thereafter enters the proximal lumen 512. Because the proximal lumen 512 is of a comparatively larger diameter than the distal lumen 510 and has smooth inner walls, the tissue specimen tends to expand, decompress and to untwist, to some degree. The specimen may then be collected from the proximal end of the cannula 500, which collection is facilitated by the larger diameter of the proximal lumen 512. A vacuum may be present within the distal and proximal lumens 510 512, and may further help retain and extract the collected specimen therein. Smaller gauge cannulas may be used to collect cells, whereas larger gauge cannulas may be utilized where large core devices are conventionally utilized. It is believed, therefore, that such a method may find utility in the retrieval of not only cellular specimens, but also in the retrieval of substantially intact tissue samples. Indeed, it is believed that the size of the cannulas shown in FIGS. 5A, 5B and 5C (as well as those shown in FIGS. 1A through 4B) may be appropriately scaled, depending upon the procedure to be carried out.

Figure 6:
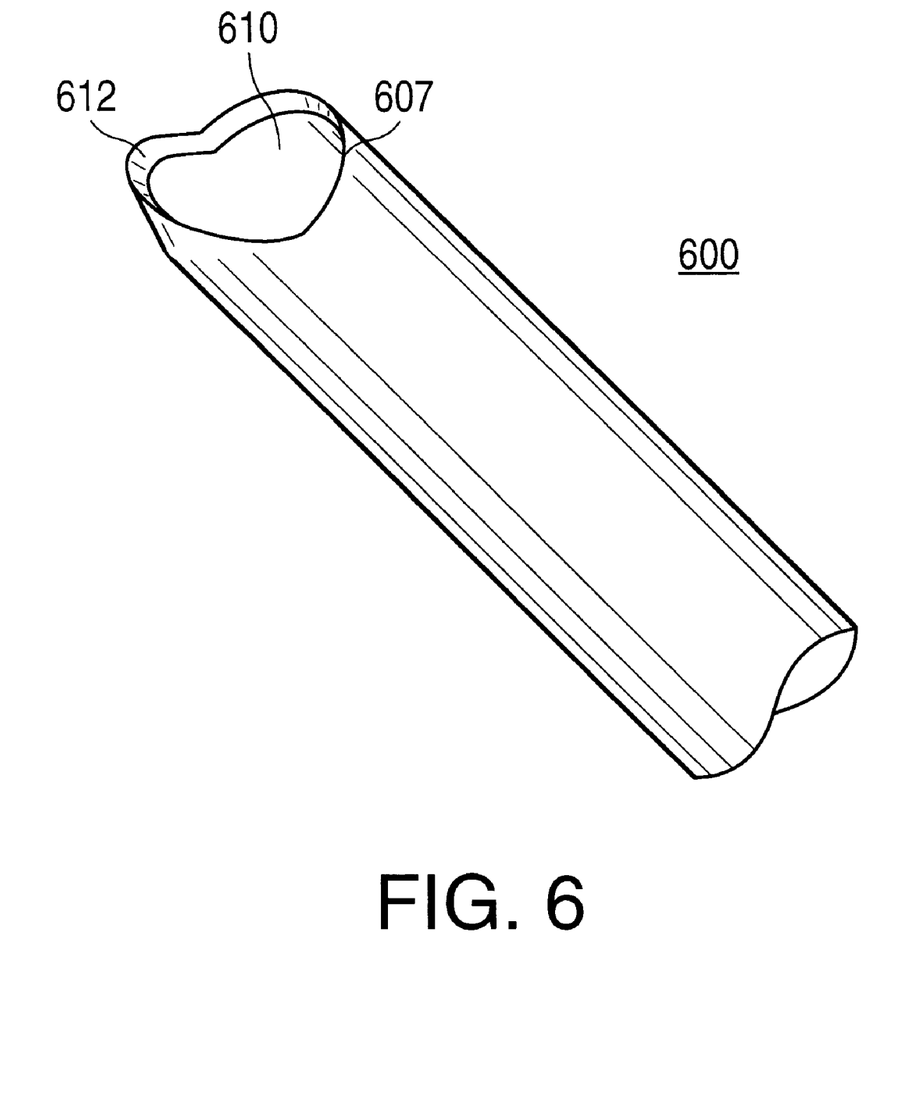
FIG. 6 is a perspective view of a device for collecting cell and/or tissue specimen, illustrating an embodiment of the distal part-off means according to the present invention.

The embodiments of the cannulas shown in FIGS. 1A through 5C may include a distal part-off means attached to the conical distal tip. An embodiment of such a part-off means is shown in FIG. 6. FIG. 6 shows a cannula 600 having a sharpened distal conical tip 607 similar to those shown in FIGS. 1A through 5C. As shown in FIG. 6, the part-off means includes a shaped portion of a sharpened semi-hemispherical member 612, which is attached to the conical distal tip 607. Alternatively, the member 612 may be integral to the cannula 600 and may be sharpened along its distal-most edge. As the cannula 600 rotates, the part-off means 612 slices at least a portion of the tissue from the base of the core, weakening or severing its attachment to the main tissue mass. Preferably, the part-off means should assist in the parting off of the specimen from the main tissue mass, but not substantially hinder the tendency of the tissue it slices to enter the lumen 610 of the cannula 600. Preferably, the part-off means 612 and the cannula 600 are made from stainless steel, a nickel-titanium alloy or other hard material.

Figure 7:
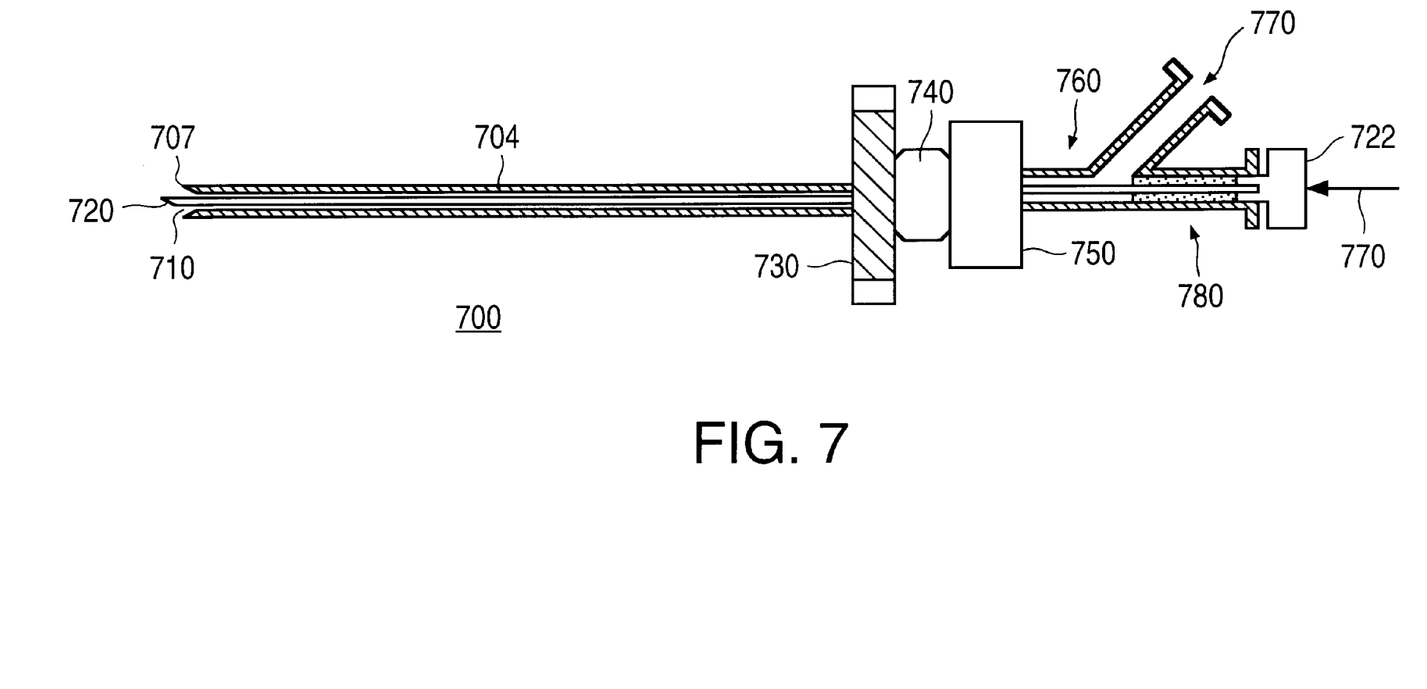
FIG. 7 is a cross-sectional view of an embodiment of the device according to the present invention.
Figure 8:
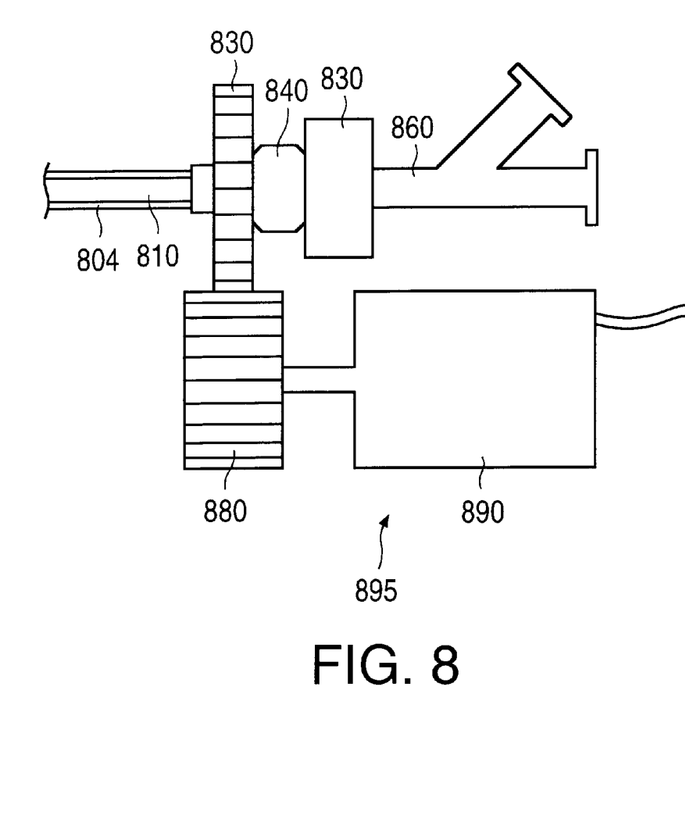
FIG. 8 is a schematic view of the proximal end of an embodiment of the present invention, illustrating an embodiment of the offset motor drive unit.

FIG. 7 shows a device 700 for retrieving a biological specimen from soft tissue, according to an embodiment of the present invention. The device 700 includes a cannula 704, shown in cross-section. The cannula 704 may include urging means (not shown), such as the urging means 102, 202, 302, 402 or 502 shown in FIGS. 1A through 4B, or a variant or combination of the urging means shown in these figures. Moreover, the cannula 704 may include the structures shown in FIGS. 5A, 5B and 5C, although these are not shown in FIG. 7 for clarity. Additionally, the cannula 704 of the device 700 may also include part-off means, such as shown in FIG. 6 at reference numeral 612, although such part-off means are also not shown in FIG. 7 for clarity. Inserted within the axial lumen 710 of the cannula 704 is a stylet 720. According to the present invention, the stylet 720 remains within the lumen 710 until the cannula 704 has reached the target lesion site, whereupon it is at least partially retracted in the proximal direction. This retraction of the stylet 720 may induce a vacuum within the lumen 710, further assisting in the collection of the specimen from the main tissue mass, such as the patient's breast. The stylet 720 may be manually retracted or may be retracted by a stylet drive unit, not shown. At a predetermined distance from the distal tip 707 of the cannula 704, which will vary according to the application envisaged, is a rotating driven gear 730. The rotating driven gear 730 imparts the rotational motion to the cannula 704 when driven by an appropriate offset motor drive unit, such as shown in FIG. 8. Preferably, to minimize run-out—that is, to insure that the cannula 704 remains axially aligned at all times, the driven gear 730 is bonded to or molded into the cannula 704. A rotating union connector 740, best shown in FIG. 8, is coupled to the driven gear 730. At the proximal end of the device 700 is a Y-shaped adapter 760. The hub 722 of the stylet 720 protrudes from the proximal end of the adapter 760, to allow easy retraction of the stylet 720 from the lumen 710 of the cannula 704. Between the rotating union connector 740 and the adapter 760 is a stationary mount 750. A seal 780, which may be a rotating valve of the Touhy-Borst type, insures that a substantially airtight seal is maintained within the lumen 710 when the stylet 720 is retracted or withdrawn from the lumen 710. Alternately, as shown in FIG. 7, the seal 780 may be a latex injection site, which automatically seals the distal end of the Y-adapter 760 upon retraction or withdrawal of the stylet 720. Finally, in the illustrative embodiment of FIG. 7, a vacuum means 770, such as a syringe, VACUTAINER® or other vacuum inducing device is attached to the non-axial branch of the Y-shaped adapter 760. For example, if a syringe is employed as the vacuum means 770, retraction of the syringe plunger induces a vacuum within the lumen 710, thereby facilitating drawing the tissue through the lumen 710 for later retrieval.

FIG. 8 shows, in simplified schematic form, the proximal end of the device of FIG. 7, mated to an offset motor drive unit 895. Indeed, the cannula 804 is bonded, molded with or otherwise attached to the driven gear 830. Between the driven gear 830 and the stationary mount 830 attached to the Y-shaped adapter 860 is the rotating union 840. The offset motor drive unit 895 includes a driving gear 880 that is in contact with and drives the driven gear 830. An electric motor 890, preferably battery operated, rotates the driving gear 880, and provides the motive force to the assembly.

Figure 9:
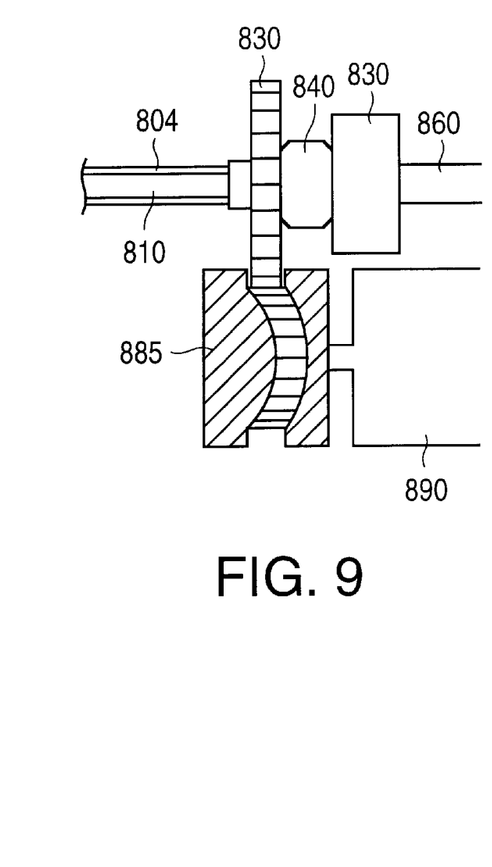
FIG. 9 is a schematic view of the proximal end of an embodiment of the present invention, illustrating an embodiment of the oscillatory drive means.

The cannula 804 may, according to a still further embodiment of the present invention, be made to axially oscillate as it is advanced and rotated through the soft tissue and/or the target lesion site. It is believed that such a reciprocal, or oscillatory motion may help to both collect tissue within the lumen 810, as well as to advance the cannula 804 through particularly dense tissue, such as fibroids or microcalcifications within breast or other soft tissue. To achieve this oscillatory motion, the driving gear 880 of FIG. 8 may be replaced by a drive gear with a sinusoidal track, as shown in FIG. 9 at reference numeral 885. In this manner, the driving gear 885 will impose a small oscillatory motion upon the cannula 804. The driving gear 880 and driven gear 830 may be replaced by a belt drive, pinch roller arrangement, or other suitable oscillatory motion inducing drive means, as those of skill will recognize.

The device for collecting biological specimens from soft tissue, according to the present invention, may readily be adapted for either manual one-handed operation or for machine operation, under stereotactic control and guidance.

In use, the cannula 704 of the device 700 of FIG. 7 according to the present invention may be inserted into the breast or other soft tissue with the stylet 720 fully engaged in the lumen 710. This insures that no tissue or cells are inadvertently collected within the lumen 710 until the target site or lesion is reached. The cannula 704 is then advanced until the distal conical tip 707 of the cannula 704 is near the target site. The motor drive unit 895, shown in FIG. 8, is then engaged, driving the driven gear 730 and rotating the cannula 704. Alternatively, the motor drive unit 895 may be engaged at the outset, and the cannula 704 may be rotated as it is advanced towards the target region. If the device includes a driving gear with a sinusoidal track 885 or other means for imposing an oscillatory motion upon the cannula 704, the cannula 704 will oscillate and rotate as it is advanced to and through the lesion. The sharpened conical distal tip 707 of the cannula 704 will then rotate and efficiently slice through the tissue, which will then readily enter the lumen 710. If present, urging means, such as the urging means of FIGS. 1A through 5B, will then twist and compress the tissue while it is drawn in the proximal direction through the lumen 710, optionally assisted by a vacuum provided by vacuum means 770. Upon stopping and/or reversing the rotation of the cannula 704, the twisted and compressed tissue will then untwist and expand somewhat, further insuring that the collected tissue specimen will remain within the lumen 710. The collected specimen may then be collected and/or the cannula may be retracted from the soft tissue mass. Although the present invention has been disclosed relative to breast biopsies, it is to be understood that the devices and methods disclosed herein are applicable to other soft tissue masses, such as the liver, lungs or thyroid gland, for example.

While the foregoing detailed description has described several embodiments of this invention, it is to be understood that the above description is illustrative only and not limiting of the disclosed invention. For example, the urging means within the lumen may differ from those illustrated in FIGS. 1A through 4B. A number of other modifications will no doubt occur to persons of skill in this art. All such modifications, however, should be deemed to fall within the scope of the present invention. Thus, the invention is to be limited only by the claims as set forth below.

What is claimed is:

1. A device to retrieve a specimen from soft tissue, comprising:

a cannula having an axial lumen and a sharpened distal tip;

discontinuous tissue urging means extending along at least a portion of a length of the axial lumen, the tissue urging means urging the specimen into and along the axial lumen upon rotation of the cannula; and drive means for rotating the cannula.

2. The device of claim 1, wherein the axial lumen comprises a distal and proximal section, the proximal section having a greater diameter than the distal section, the tissue urging means extending along at least a portion of a length of the distal section of the axial lumen.

3. The device of claim 1, wherein the drive means comprises means for axially oscillating the cannula during rotation thereof.

4. The device of claim 1, further comprising a stylet adapted to fit within the axial lumen of the cannula.

5. The device of claim 1, wherein the discontinuous tissue urging means is disposed in a generally spirally shaped configuration about a circumference of the axial lumen.

6. The device of claim 1, wherein the discontinuous tissue urging means includes a plurality of through cut slots.

7. The device of claim 1, wherein the discontinuous tissue urging means includes one of discontinuous raised features rising from an interior surface of the axial lumen and discontinuous spiral threading within the axial lumen.

8. The device of claim 1, wherein the tissue urging means includes spirally wound deformations in both an outer surface of the cannula and in the axial lumen thereof.

9. The device of claim 1, further comprising a part-off means attached to the distal tip.

10. The device of claim 9, wherein the part-off means includes a portion of a sharpened semi-hemispherical member fitted to the distal tip.

11. A device to retrieve a specimen from soft tissue, comprising:

a cannula having an axial lumen, the axial lumen including a distal section, a proximal section and a transitional section between the distal and proximal sections, the proximal section having a greater diameter than the distal section such that the transitional segment forms an angle $\Theta$ selected between about 1 and about 20 degrees with respect to the proximal section and the distal section; and tissue urging means integral to the cannula and extending along at least a portion of a length of the distal section of the axial lumen, the tissue urging means urging the biological specimen first into the distal section and then into the proximal section upon rotation of the cannula.

12. The device of claim 11, wherein the tissue urging means is discontinuous.

13. The device of claim 11, wherein the tissue urging means is continuous.

14. The device of claim 11, wherein the tissue urging means is disposed in a generally spiral-shaped configuration about a circumference of the cannula.

15. The device of claim 11, wherein the tissue urging means includes a plurality of through cut slots.

16. The device of claim 11, wherein the tissue urging means includes spiral threading of the axial lumen of the cannula.

17. The device of claim 16, wherein a pitch of the spiral threading is selected within a range of about 10 to about 300 threads per inch.

18. The device of claim 11, wherein the tissue urging means includes a spirally wound raised feature rising from a surface of the axial lumen.

19. The device of claim 11, wherein the tissue urging means includes spirally wound deformations in both an outer surface of the cannula and in the axial lumen thereof.

20. The device of claim 11, further comprising a part-off means attached to a distal tip of the distal section.

21. The device of claim 20, wherein the part-off means includes a portion of a sharpened semi-hemispherical member.

22. The device of claim 11, further including a stylet adapted to fit within the axial lumen.

23. The device of claim 11, further comprising:
an adapter connected to a proximal end of the cannula; and
vacuum means for creating a vacuum within the axial lumen, the vacuum means being attached to the adapter.

24. The device of claim 11, further including a motorized drive means to selectively rotate the cannula.

25. The device of claim 24, wherein the drive means comprises means for axially oscillating the cannula upon rotation thereof.

26. The device of claim 11, wherein a distal tip of the distal section is sharpened on an outer diameter of the cannula.

27. The device of claim 11, wherein a distal tip of the distal section is sharpened on an inner diameter of the cannula.

28. A soft tissue biopsy method, comprising the steps of:
advancing a rotating cannula-stylet combination into a mass of soft tissue, the cannula having a distal center lumen and a proximal center lumen aligned with the distal lumen, a diameter of the proximal lumen being larger than a diameter of the distal lumen;

at least partially retracting the stylet when the combination is near a target site within the soft tissue;

twisting and compressing the tissue within the distal lumen as the tissue progresses through the distal lumen upon rotation and advancement of the cannula to and through the target site;

at least partially untwisting and decompressing the twisted and compressed tissue as the tissue enters the proximal lumen; and collecting the expanded tissue from the proximal lumen.

29. The method of claim 28, further comprising the step of at least partially parting-off the twisted tissue prior to stopping the rotation of the cannula.

30. The method of claim 29, wherein the parting-off step includes a step of macerating tissue at a distal tip of the cannula by stopping the advancement of the cannula through the mass of soft tissue while continuing the rotation thereof.

31. The method of claim 28, further comprising the step of imposing an oscillating axial movement on the cannula as the cannula rotates and advances through the target site.

* * * * *